(12) United States Patent
Butoyi

(10) Patent No.: US 8,060,258 B2
(45) Date of Patent: Nov. 15, 2011

(54) MULTIVARIABLE PROCESS CONTROLLER AND METHODOLOGY FOR CONTROLLING CATALYZED CHEMICAL REACTION TO FORM PHTHALIC ANHYDRIDE AND OTHER FUNCTIONALIZED AROMATICS

(75) Inventor: Firmin Butoyi, Terneuzen (NL)

(73) Assignee: Honeywell International Inc., Morristown, NJ (US)

( * ) Notice: Subject to any disclaimer, the term of this patent is extended or adjusted under 35 U.S.C. 154(b) by 1144 days.

(21) Appl. No.: 11/770,142

(22) Filed: Jun. 28, 2007

(65) Prior Publication Data

US 2009/0005908 A1     Jan. 1, 2009

(51) Int. Cl.
*G05B 21/00* (2006.01)
*B01J 10/00* (2006.01)

(52) U.S. Cl. .................. 700/266; 700/268; 422/129

(58) Field of Classification Search .................. 700/266, 700/268; 422/129
See application file for complete search history.

(56) References Cited

U.S. PATENT DOCUMENTS 6,380,399 B1    4/2002  Okuno et al.
2003/0073787 A1  4/2003  Stephens et al.

*Primary Examiner* — Brian J Sines
(74) *Attorney, Agent, or Firm* — Jetter & Associates, P.A.

(57) ABSTRACT

A multivariable method and process controller is for controlling a catalyzed chemical reaction to form phthalic anhydride (PA), produced by a production unit including a chemical reactor having a plurality of pipes connected in parallel having inner surfaces affixed with at least one solid catalyst. The reactor implements a process for forming PA by receiving flows of reagents including at least one oxidizable substituted aromatic and an oxygen including source gas at one or more inlets of the reactor. A dynamic multivariable model for the process represents the effects of moving a plurality of manipulated variables (MVs) including a flow of the oxygen including source gas and a flow or temperature of the oxidizable substituted aromatic on controlled variables (CVs) including a temperature at a plurality of positions along a length of the pipes. During the process, a first parameter related to performance of the catalyst in producing PA and a second parameter including a temperature at one or more of the plurality of positions in measured. Using the dynamic model, the temperature in the plurality of positions along the length of the reactor are automatically adjusting based on at least the first measured parameter, which permits the temperature profile to be adjusted to compensate for ageing of the catalyst to improve production efficiency.

7 Claims, 17 Drawing Sheets

|   | DESCRIPTION | UNITS |
|---|---|---|
| 1 | F14E AIR FLOW | $Nm^3/h$ |
| 2 | ORTHOXYLENE FLOW THROUGH E12D | kg/hr |
| 3 | ORTHOXYLENE FLOW THROUGH E12E | kg/hr |
| 4 | NAPHTHALENE FLOW THROUGH E12B | kg/hr |
| 5 | NAPHTHALENE FLOW THROUGH E12C | kg/hr |
| 6 | NAPHTHALENE EVAPORATOR B OUTLET TEMPERATURE | Deg C |
| 7 | NAPHTHALENE EVAPORATOR C OUTLET TEMPERATURE | Deg C |
| 8 | SALT BATH TEMPERATURE | Deg C |

FIG. 7

|  | DESCRIPTION | UNIT |
|---|---|---|
| 1 | TOTAL AIR FLOW | $Nm^3/hr$ |
| 2 | MAIN AIR BLOWER CURRENT | A |
| 3 | TOTAL REACTANT CONCENTRATION | $g/Nm^3$ |
| 4 | SINGLEPOINT TEMPERATURE TID142 | Deg C |
| 5 | SINGLEPOINT TEMPERATURE TID143 | Deg C |
| 6 | SINGLEPOINT TEMPERATURE TID144 | Deg C |
| 7 | SINGLEPOINT TEMPERATURE TID145 | Deg C |
| 8 | SINGLEPOINT TEMPERATURE TID146 | Deg C |
| 9 | SINGLEPOINT TEMPERATURE TID147 | Deg C |
| 10 | SINGLEPOINT TEMPERATURE TID148 | Deg C |
| 11 | CRUDE PRODUCTION | Kg/hr |
| 12 | O-XYLENE D CONCENTRATION TO F14D | $g/Nm^3$ |
| 13 | O-XYLENE E CONCENTRATION TO F14E | $g/Nm^3$ |
| 14 | NAPHTHALENE B CONCENTRATION OUT OF E12B | $g/Nm^3$ |
| 15 | NAPHTHALENE C CONCENTRATION OUT OF E12C | $g/Nm^3$ |
| 16 | TOTAL OXIDE CONCENTRATION BEFORE F14B | $g/Nm^3$ |
| 17 | TOTAL OXIDE CONCENTRATION BEFORE F14C | $g/Nm^3$ |
| 18 | TOTAL OXIDE CONCENTRATION DIFFERENCE (F14B-F14C) | $g/Nm^3$ |
| 19 | NAPHTHALENE FLOW E12B/E12C DIFFERENCE | Kg/hr |
| 20 | TOTAL NAPHTHALENE CONSUMED PER DAY | T |
| 21 | TOTAL OXYLENE CONSUMED PER DAY | T |
| 22 | NAPHTHALENE FLOW CONTROLLER E12B CONTROLLER | % |
| 23 | NAPHTHALENE FLOW CONTROLLER E12C CONTROLLER OUTPUT | % |
| 24 | O-XYLENE D FLOW CONTROLLER VALVE OUTPUT | % |
| 25 | O-XYLENE E FLOW CONTROLLER VALVE OUTPUT | % |
| 26 | F14E AIR FLOW CONTROLLER OUTPUT | % |
| 27 | CVRESERVE1 |  |
| 28 | CVRESERVE2 |  |

|  | DV |  |  |
|---|---|---|---|
| 1 | AMBIENT TEMPERATURE | T61158XI.PV | DEG C |

FIG. 8

| CONTROLLER DETAIL | | ON | OFF | WARM | APP MENU | OPTIONS | STATUS MSGS | REPORT | |
|---|---|---|---|---|---|---|---|---|---|
| CV SUMMARY | CV DETAIL | | CV OPTIMIZE | | CV CONTROL | CV PROCESS | CV ADV TUNING | GAIN DELAY | |
| MV SUMMARY | MV DETAIL | | MV OPTIMIZE | | MV CONTROL | MV PROCESS | DV SUMMARY | DV DETAIL | |
| | | | | | MOVE DOWN | MOVE UP | MOVE TO TOP | BY CV # | |

| CV # | CV DESCRIPTION | STATUS | VALUE | FUTURE | SS VALUE | LO LIMIT | HI LIMIT | SET POINT |
|---|---|---|---|---|---|---|---|---|
| 1 | TOTAL AIR FLOW | GOOD | 55601 | 55588 | 55588 | 54500 | 55800 | |
| 2 | MAIN AIR BLOWER CURRENT | GOOD | 124.7 | 124.7 | 124.7 | 0 | 135.0 | |
| 3 | TOTAL REACTANT CONCENTRATION | GOOD | 80.57 | 80.63 | 80.64 | 0 | 81.00 | |
| 4 | SINGLEPOINT TEMPERATURE TID142 | DROP | 409.3 | 402.0 | 402.0 | 300.0 | 455.0 | |
| 5 | SINGLEPOINT TEMPERATURE TID143 | DROP | 412.4 | 406.3 | 406.3 | 300.0 | 455.0 | |
| 6 | SINGLEPOINT TEMPERATURE TID144 | DROP | 409.6 | 404.8 | 404.8 | 300.0 | 455.0 | |
| 7 | SINGLEPOINT TEMPERATURE TID145 | GOOD-C | 441.2 | 441.5 | 441.5 | 300.0 | 444.0 | |
| 8 | SINGLEPOINT TEMPERATURE TID146 | DROP | 451.1 | 439.8 | 439.8 | 300.0 | 457.0 | |
| 9 | SINGLEPOINT TEMPERATURE TID147 | GOOD | 429.9 | 430.0 | 430.0 | 300.0 | 435.0 | |
| 10 | SINGLEPOINT TEMPERATURE TID148 | GOOD | 428.5 | 428.7 | 428.7 | 300.0 | 432.0 | |
| 11 | CRUDE PRODUCTION | GOOD | 4442. | 4442 | 4442 | 2000. | 5000. | |
| 12 | O-XYLENE D CONCENTRATION TO F14D | GOOD | 24.24 | 24.25 | 24.25 | 0 | 33.00 | |
| 13 | O-XYLENE E CONCENTRATION TO F14E | GOOD | 30.42 | 30.41 | 30.41 | 0 | 33.00 | |
| 14 | NAPHTHALENE B CONCENTRATION OUT OF E12B | GOOD | 61.76 | 61.80 | 61.82 | 0 | 66.00 | |
| 15 | NAPHTHALENE C CONCENTRATION OUT OF E12C | GOOD | 44.86 | 45.00 | 44.99 | 0 | 45.50 | |
| 16 | TOTAL OXIDE CONCENTRATION BEFORE F14B | GOOD | 85.99 | 86.05 | 86.07 | 68.00 | 86.50 | |
| 17 | TOTAL OXIDE CONCENTRATION BEFORE F14C | GOOD | 75.28 | 75.39 | 75.38 | 60.00 | 86.00 | |
| 18 | TOTAL OXIDE CONCENTRATION DIFFERENCE (F14B-F14C) | GOOD | 10.69 | 10.75 | 10.78 | -10.00 | 11.00 | |
| 19 | NAPHTHALENE FLOW F12B/E12C DIFFERENCE | GOOD | 428.8 | 429.0 | 430.0 | 290.0 | ◇ 430.0 | |
| 20 | TOTAL NAPHTHALENE CONSUMED PER DAY | GOOD | 71.10 | 71.10 | 71.10 | 0 | ◇ 71.10 | |
| 21 | TOTAL OXYLENE CONSUMED PER DAY | GOOD | 36.50 | 36.50 | 36.50 | 36.50 | 36.50 | 36.50 |
| 22 | NAPHTHALENE FLOW CONTROLLER E12B CONTROLLER | GOOD | 45.92 | 45.95 | 45.96 | 0 | 49.00 | |
| 23 | NAPHTHALENE FLOW CONTROLLER E12C CONTROLLER OUTPUT | GOOD | 38.38 | 38.26 | 38.26 | 0 | 48.00 | |
| 24 | O-XYLENE D FLOW CONTROLLER VALVE OUTPUT | GOOD | 83.97 | 83.96 | 83.96 | 0 | 94.00 | |
| 25 | O-XYLENE E FLOW CONTROLLER VALVE OUTPUT | GOOD | 96.69 | 96.70 | 96.70 | 0 | 100.0 | |
| 26 | F14E AIR FLOW CONTROLLER OUTPUT | GOOD | 83.34 | 83.36 | 83.36 | 0 | 88.00 | |
| 27 | ORTHOXYLENE FLOW DIFFERENCE THROUGH F14D AND F14E | GOOD | -189.2 | -189.2 | -189.2 | -200.0 | -130.0 | |
| 28 | CVRESERVE2 | DROP | 0 | 5.795 | 5.795 | -1.000 | 1.000 | |

FIG. 10 CONTROLLED VARIABLES DISPLAY

| CONTROLLER DETAIL | | ON | OFF | WARM | APP MENU | OPTIONS | STATUS MSGS | | REPORT |
|---|---|---|---|---|---|---|---|---|---|
| CV SUMMARY | CV DETAIL | CV OPTIMIZE | | | CV CONTROL | CV PROCESS | CV ADV TUNING | | GAIN DELAY |
| MV SUMMARY | MV DETAIL | MV OPTIMIZE | | | MV CONTROL | MV PROCESS | DV SUMMARY | | DV DETAIL |
| | | | | | MOVE DOWN | MOVE UP | MOVE TO TOP | | BY MV # |

| MV # | MV DESCRIPTION | STATUS | VALUE | MOVE | FUTURE | SS VALUE | LO LIMIT | HI LIMIT | MODE |
|---|---|---|---|---|---|---|---|---|---|
| 1 | F14E AIR FLOW | ON | 25949 | 0 | 25949 | 25949 | 24000 | 26700 | RMPC |
| 2 | ORTHOXYLENE FLOW THROUGH E12D | ON | 665.8 | 0 | 665.8 | 665.8 | 200.0 | 800.0 | RMPC |
| 3 | ORTHOXYLENE FLOW THROUGH E12E | ON | 855.0 | 0 | 855.0 | 855.0 | 200.0 | 855.0 | RMPC |
| 4 | NAPHTHALENE FLOW THROUGH E12B | ON | 1696. | 0.0144 | 1696. | 1696. | 500.0 | 1750. | RMPC |
| 5 | NAPHTHALENE FLOW THROUGH E12C | ON | 1267. | -0.0129 | 1267. | 1266. | 500.0 | 1700. | RMPC |
| 6 | NAPHTHALENE EVAPORATOR B OUTLET TEMPERATURE | ON | 138.5 | 0 | 138.5 | 138.5 | 138.5 | 139.5 | RMPC |
| 7 | NAPHTHALENE EVAPORATOR C OUTLET TEMPERATURE | ON | 140.6 | 0 | 140.6 | 140.6 | 140.0 | 141.0 | RMPC |
| 8 | SALT BATH TEMPERATURE | ON | 373.0 | 0 | 373.0 | 373.0 | 372.8 | 373.2 | RMPC |

FIG. 11(a):
MANIPULATED VARIABLES DISPLAY

MANIPULATED VARIABLES TIME PLOT WITHOUT (LEFT) AND WITH (RIGHT) THE INVENTIVE SOLUTION IN PLACE

REACTOR TEMPERATURES CV'S, THE BOTTOM 3 VARIABLES ARE NOW CONTROLLED

PRODUCTS AND RAW MATERIAL CV'S

CONCENTRATION CV's

REACTANT FLOW CONTROLLER VALVE POSITION TIME PLOT WITHOUT (LEFT) AND WITH (RIGHT) THE INVENTIVE SOLUTION.

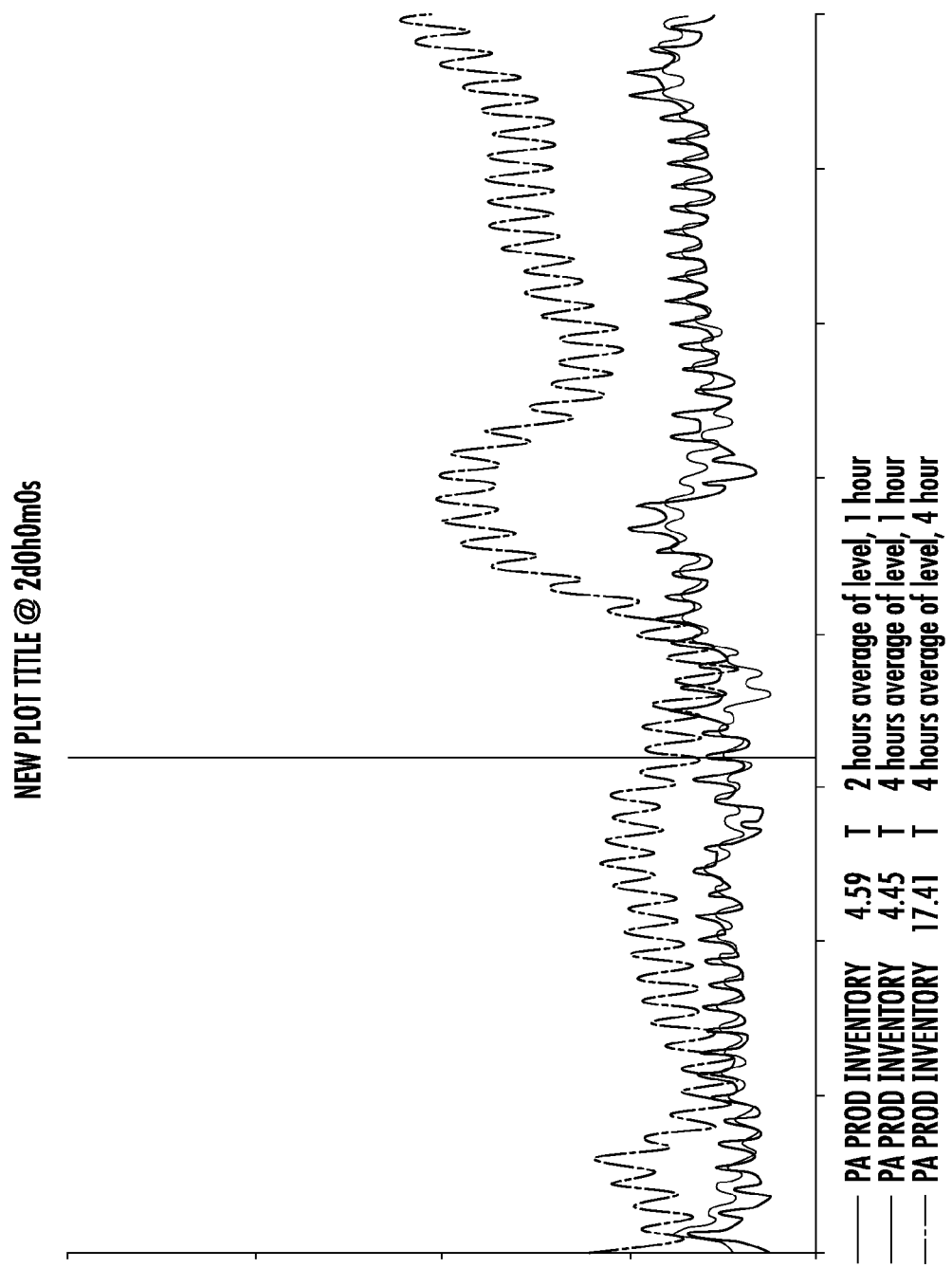

MULTIVARIABLE PROCESS CONTROLLER AND METHODOLOGY FOR CONTROLLING CATALYZED CHEMICAL REACTION TO FORM PHTHALIC ANHYDRIDE AND OTHER FUNCTIONALIZED AROMATICS

FIELD OF THE INVENTION

The present invention relates to a multivariable control methodology and related multivariable process controllers for controlling a chemical reaction having a fixed catalyst subject to aging for production processes which form functionalized aromatics, such as phthalic anhydride.

BACKGROUND

Phthalic anhydride (PA) is widely used in industry in the production of dyes (rhodamine, anthraquinone derivatives), insecticides, plasticizers, in pharmacy, and in analytic chemistry. PA is conventionally prepared industrially by catalytic gas-phase oxidation of orthoxylene or naphthalene in shell-and-tube reactors. The starting material is a mixture of a gas comprising oxygen, such as air, and the orthoxylene and/or naphthalene to be oxidized. The mixture is passed through a multiplicity of tubes arranged in a reactor (shell-and-tube reactor), in each of which a bed of at least one catalyst is located. Known PA catalysts include vanadium oxide and titanium oxide as active ingredients supported on an inert carrier. The production of PA from orthoxylene and naphthalene is cheaper compared to other processes for forming PA, and selling extra PA product is generally not a limitation.

An exemplary conventional PA production system ("PA unit") is described below which comprises air blower (G-11) and air preheater (E-11) section (see FIG. 1; described below), an orthoxylene feed section (see FIG. 2; described below), a naphthalene feed section (See FIG. 3; described below), and a catalytic oxidation reactor section including D-14 oxidizing reactor (see FIG. 4; described below). The exemplary PA unit also includes a cooling of reactor gases (E16) section and desublimation of PA section (E-18A, B and C, D; (see FIG. 5; described below), and catalytic incineration of waste gases (R111) section (see FIG. 6; described below).

Referring now to FIG. 1, an air blower and preheater section 100 is depicted. Turbo-blower G-11 sucks and compresses the amount of oxidizing air necessary for the reactor D-14 via air filter F-11. The air is heated up in the steam-heated air pre-heater E-11 to a temperature of approximately 160° C. The air flow measurements on the flows going to the evaporators and to the reactor are doubled on both lines. In a conventional case, doubling is used as shown in FIG. 1. The air-cooling capacity is generally not a limitation. The incoming air flow valve is adjusted to maintain a wanted air flow through F-14E air-orthoxylene mixer (shown and described in FIG. 2). The blower current is generally a very important variable for the operators and is used and an indication of the turbo blower load. After the pre-heater E-11, the flow of air is distributed into 4 branches, D-14B, D-14C, E-12B and E-12C.

FIG. 2 show an orthoxylene feed section 200. The two main air ducts convey the oxidizing air into mixers F-14D and E. In this place orthoxylene is injected into the flow of air. The generated mixture of air and orthoxylene vapors is conveyed into gas mixers F-14 B and C, respectively. The main flow mixtures of air are mixed there with the air saturated with naphthalene flumes after having passed through evaporators E-12 B and C (shown in FIG. 3, described below). The obtained mixture of air, naphthalene and orthoxylene fumes is then conveyed into the oxidizing reactor D-14, shown in FIG. 4 as reactor 400. The incoming orthoxylene flow is controlled according to the orthoxylene concentration after F-14D and E, the units generally being in $g/Nm^3$.

FIG. 3 shows a naphthalene feed section 300. A small portion of air is aspirated by auxiliary turbo-blower G-13 and it is conveyed as carrier gas through naphthalene evaporators E-12 B and C where it is saturated with naphthalene. The required concentration of naphthalene is set according to the temperature of air at the outlet, which is regulated to the required temperature by means of the heating steam. This concentration generally exceeds the upper explosion limit.

The concentrated mixture of naphthalene and air is mixed in gas mixers F-14 B and C with the main flow of air containing orthoxylene and thus the concentration is set to the required value above the lower explosion limit of the mixture (e.g. 45 $g/Nm^3$) TN-OX in the air. To admit orthoxylene, two orthoxylene, air mixers F-14 D and E (as shown in FIG. 2) are installed after the intake of the partial airflow for the naphthalene evaporators and ahead of gas mixer F-14 B and C. In these apparatus, the oxidizing air is enriched with orthoxylene injected under pressure by spray nozzle. For safety reasons, the upper explosion limit is set a little under the lower explosion limit.

The naphthalene is continuously pumped from a naphthalene storage tank (not shown) by one a centrifugal pumps (not shown) via one of two filters to naphthalene evaporators E-12 B and C. The still undivided stream of naphthalene passes through a tubular heat exchanger (not shown) where it is preheated by steam to the required temperature. Following the distribution, each partial flow is controlled by the regulator according to the level in the naphthalene evaporator. Orthoxylene is continuously conveyed from an orthoxylene tank (not shown) by a centrifugal pumps (not shown) via double filter F-13 B and C into preheaters E-12 D and E and then into orthoxylen—air mixers F-14 D and E. Each partial flow is controlled depending on the actual amount of the oxidizing air. After leaving mixers F-14B and C, both streams of main air are put together and mixed in the static mixer.

Every tank of the naphthalene and the orthoxylene is analyzed, generally about once per week. The quantity of the naphthalene incoming flow is set by the E-12B and C levels, but there is no measurement, only a sideglass. F-13C cyclone can be overloaded, and if so, the temperature has to be increased. The evaporators outlet temperatures (TCxxB and C) are very important and are generally controlled adequately by the steam.

The incoming air to the evaporators (and thus the total air flow) is controlled according to a single parameter being the naphthalene concentration after F-13 B and C. The respective set points are shown as NaB[ ] and NaC[ ] in FIG. 3. The total aromatic concentration before F-14B and C should be nearly equal. After mixing the B and C lines, the concentrations are: FKNAA2 for naphtha, FKOXA2 for orthoxylene and FKNOA2 for the summary of the two. This last value should not exceed about 85 $g/m^3$, but the limit depends on the ratio of naphthalene to orthoxylene.

Referring to catalytic oxidation reactor 400 shown in FIG. 4, in the standard operation, the mixture of naphthalene and orthoxylene vapors and air within the explosion limits occurs under the upper reactor cover, in the mixers and, in the starting operation, for a limited period of time, also in the naphthalene evaporators. The naphthalene and orthoxylene mixture enters the reactor D-14 from above and exits from below as shown by the arrows in FIG. 4. The reactor conventionally includes about 14,000 vertical pipes connected in parallel which are about 3.7 m. long, which are filled with a highly efficient 4-layer oxidation catalyst. The tubes are surrounded by salt bath, generally comprising a eutectic mixture of potassium nitrate and sodium nitrite, which is continuously re-circulated by pump G-14. The mixture of naphthalene and orthoxylene vapors entering the rector at a temperature of 145 to 150° C. is first heated up to the heat of reaction by the molten salt. At a temperature of 360 to 390° C., naphthalene and orthoxylene are partially catalytically oxidized by the atmospheric oxygen mainly to the desired PA product.

A smaller portion of naphthalene is at the same time converted to 1,4maleic anhydride, or it is completely oxidized (to carbon dioxide and water). If the heat of reaction is too low, a greater amount of 1,4naphtaquinone is produced. If the temperature is too high, the proportion of maleic anhydride increases and the major part of naphthalene is completely oxidized. A part of orthoxylene is also converted to maleic anhydride or it undergoes complete oxidation. As a by-product of partial orthoxylene oxidation, phthalate is produced.

The oxidation reactions catalyzed by the catalyst are very exothermic. By means of suitable in-built structures and by recirculating salt bath G-14, the temperature in the reactor is distributed in a uniform manner. The heat of reaction is removed from the salt bath by the evaporation of condensate in evaporator E-14, where a mixture of steam and water is produced. The mixture of steam and water is conveyed into a high-pressure steam drum (not shown), where it is separated into saturated steam and condensate.

The pressure in the reactor cooling system is maintained stable by means of a controlling valve set at a value higher than the usual pressure in the plant system. The hot spot profile can change by changing the concentration. Temperatures at various positions along the height of reactor 400 are provided as single point temperature in the catalyst "layers" TID142-TID148. The highest temperature position should be between about 150-200 cm from the reactor top, it can be controlled by controlling the TID148 temperature that should generally never go above 420 C. The speed of temperature changing is also generally important, but it is not critical.

The temperature of salt bath G-14 temperature can generally vary ±0.25° C. in stable operation. By increasing the salt bath temperature the catalyst temperature will decrease, by decreasing the salt bath temperature, the catalyst temperature will increase. This is a direct way of controlling the highest catalyst temperature. Changing of the salt bath temperature does not change the production, only the lifetime of the catalyst.

The stream of the reaction gas let out from the lower part of reactor D-14 is conveyed into the common housing of two-stage cooler E-16, where the heat contained in the gas is used for the generation of steam. The cooler proper comprises four sections of vertical finned tubes. The first two sections are connected by means of piping with a steam drum (not shown) and the remaining sections with another steam drum (not shown).

In the first two bundles, the boiler water from drum changes into a mixture of steam and water and due to the thermosiphon effect, it is conveyed back to the drum, in which the steam is separated and conveyed for further use. In a similar manner, the third and the fourth cooler bundles are interconnected with a drum.

FIG. 5 shows a desublimation of phthalic anhydride section 500. The reaction gas gradually cooled down in cooler E-16 is further cooled in desublimators E-18 A-D. The desublimator comprises four heating bodies consisting of finned tubes located in a common housing. The reaction gas enters the desublimator from above and it is cooled down. In the course of the cooling process, phthalic anhydride is deposited on the fins of the tubes in the form of rod-like crystals with an efficiency of up to 99.5%. After the phthalic anhydride is isolated, the reaction gas turns into waste gas, which is conveyed to catalytic incinerator for final purification.

FIG. 6 shows a catalytic incineration of waste gases section 600. The flow of gases from desublimators E-18A through D shown in FIG. 5 contains residues of organic matter which have not been isolated (PA, maleic anhydride, etc.), carbon monoxide and carbon dioxide. These substances, in addition to the already present carbon dioxide, have to be catalytically incinerated to obtain carbon dioxide and water. Thus, undesirable emission of pollutants is prevented when waste gases are exhausted from the phthalic anhydride production plant to the atmosphere.

The waste gases are conveyed from the outlet of desublimators E 18A through D to the catalytic incinerator 600. The waste gas is first conveyed to steam pre-heater E-111 in which it is heated up by means of tubular heat exchanger heated up by steam. The waste gas then flows inside the heat exchanger E-112 tubes where it is pre-heated by counter-current by the clean waste gas to a temperature sufficient for the combustion function of the catalyst. The hot waste gas is then conveyed from heat exchanger E-112 to reactor R-111 fitted with a platinum catalyst in two levels on a ceramic carrier.

On the inner surface of the ceramic carrier bricks provided with a layer of platinum catalyst, all the organic substances and carbon monoxide will be incinerated. In the course of incineration, heat is released and thus the temperature of waste gases increases. The uncontaminated waste gas is exhausted to chimney C-81 via heat exchanger E-112.

If necessary (when the raw materials throughput in reactor D-14 is low), the temperature of waste gases in front of the heat exchanger E-112 will be increased in such a manner that it be sufficient for preheating the untreated waste gas before its entry on the catalyst. A part of the uncontaminated waste gas is therefore conducted to gas furnace C-111, where the waste gas is mixed with hot combustion gases of the gas burner.

If the supply of combustible substances is very high, the danger of catalyst overheating in reactor R-111 is imminent and if the heat transmission in heat exchanger E-112 is reduced, chimney C-81 may be overheated. In such a case, the autothermic operating mode takes place and no earth-gas is burnt down in furnace C-111. It is generally necessary to ensure continuous operation of a fan of the air of combustion (not shown) to prevent the corrosion of colder parts of the furnace by sulphur oxides.

The catalytic incinerator of waste gases is also used to decontaminate other gaseous emissions, such as from technical naphthalene, orthoxylene, naphthalene residues, pure phthalic anhydride complete with the filling condition of the truck tanks, exhaustion of the tank for the discharge of the distillation residue and the supply of waste gases from the adjacent naphthalene production plant.

Maximization in the PA production process refers to the attempt to get more PA out of the PA unit. Throughput for the PA unit is conventionally maximized using a process controller subject to a plurality of maximization constraints including a maximum air compressor flow, a maximum reactant concentration at the oxidation reactor inlet, a maximum orthoxylene concentration below low explosive level in the feeding section, a maximum naphthalene concentration above high explosive level in the feeding section, a maximum oxidation reactor catalyst temperature, and a maximum waste gas catalytic incinerator differential temperature (outlet-inlet). All of these maximization constraints are limitation factors for the conventional PA unit. As a result, once the first of the plurality of constraints become active (are reached), the maximization (attempt to get more PA out of the PA unit) process is stopped.

Moreover, present control methodologies implemented by commercially available process controllers generally manipulate only a single manipulated variable (MV) to control another variable, referred to as a controlled variable (CV). As noted above, for example, the incoming air to the evaporators, and thus the total air flow, is a CV that is controlled according to only the naphthalene concentration after F-13 B and C, a single MV (see FIG. 3). Conventional single variable control methodologies thus limit the obtainable conversion efficiency into PA product. What is needed for improving conversion efficiency is a multivariable controller that manipulates a set of MVs to maintain a set of CVs within constraints or targets. Such a multivariable control methodology would allow PA unit maximization to continue after the first constraint activation occurs.

SUMMARY

This Summary is provided to comply with 37 C.F.R. §1.73, requiring a summary of the invention briefly indicating the nature and substance of the invention. It is submitted with the understanding that it will not be used to interpret or limit the scope or meaning of the claims.

A multivariable method and process controller is for controlling a catalyzed chemical reaction to form phthalic anhydride (PA), produced by a production unit including a chemical reactor including a plurality of pipes connected in parallel having inner surfaces affixed with at least one solid catalyst. The reactor implements a process for forming PA product by receiving flows of reagents including at least one oxidizable substituted aromatic and an oxygen including source gas at one or more inlets of the reactor. A dynamic multivariable model for the process represents the effects of moving a plurality of manipulated variables (MVs) including a flow of the oxygen including source gas and a flow or temperature of the oxidizable substituted aromatic on controlled variables (CVs) including a temperature at a plurality of positions along a length of the pipes. During the process, a first parameter related to performance of the catalyst in producing the PA product and a second parameter including a temperature at one or more of the plurality of positions is measured. Using the dynamic model, the temperature in the plurality of positions along the length of the reactor are automatically adjusted based on at least the first measured parameter, which permits the temperature profile to be dynamically adjusted to compensate for ageing of the catalyst to improve production efficiency.

The first measured parameter can comprise conversion efficiency into the product. The method can further comprise the step of controlling a residence time of the reagents in the reactor by minimizing a flow rate of the oxygen comprising source gas and maintaining a sufficient flow rate of the oxygen comprising source gas to achieve a predetermined minimum for the conversion efficiency. The oxidizable substituted aromatic can comprise at least one of orthoxylene and naphthalene.

The method can further comprise the step of generating the model during step tests of the reactor by measuring values of the CVs responsive to changes in the MVs using a plurality of different test signals. The measuring values step can further comprise the step of measuring an ambient temperature. The test steps can provide data which relates the temperature in the plurality of positions and the MVs. The MVs can further comprise one or any combination of a flow of naphthalene, a flow of orthoxylene, a flow of the oxygen comprising source gas, an evaporator temperature associated with the naphthalene or orthoxylene, and a salt bath temperature associated with the reactor.

The dynamic model preferably coordinates movement the MVs with a quadratic program (QP) to meet user input control and optimization objectives, the objectives comprising the MVs and CVs. However, a linear program (LP), or a combination of a LP and QP can also be used. The measuring step can includes measuring a flow of the oxygen comprising source gas, the measuring the flow of the oxygen comprising gas further comprising the step of Kalman filtering data associated with the flow of the oxygen comprising gas.

A multivariable process controller for controlling a catalyzed chemical reaction performed in a production unit which comprises a reactor feed section and a chemical reactor comprising a plurality of pipes connected in parallel having inner surfaces affixed with at least one solid catalyst, the reactor implementing a process for forming PA by receiving flows of reagents including at least one oxidizable substituted aromatic and an oxygen comprising source at an at least one inlet of the reactor. The controller comprises a CPU having a stored dynamic multivariable model for the process which represents the effects of moving a plurality of manipulated variables (MVs) comprising a flow of the oxygen comprising source gas and a flow or temperature of the oxidizable substituted aromatic on controlled variables (CVs) comprising a temperature at a plurality of positions along a length of the pipes. A plurality of inputs are coupled to the CPU for receiving process information during the process comprising a first measured parameter related to performance of the catalyst in producing the PA product and a second measured parameter comprising the temperature at the plurality of positions. A plurality outputs are driven by the CPU for sending control signals to adjust the temperature in the plurality of positions depending on at least the first measured parameter using the dynamic model.

The first measured parameter can comprise conversion efficiency into the product. The process controller can control a residence time of the reagents in the reactor by minimizing a flow rate of the oxygen comprising source gas and maintaining a sufficient flow rate of the oxygen comprising source gas to achieve a predetermined minimum for the conversion efficiency. The process information can further comprises an ambient temperature.

The data to compile the model can be derived in part by empirical test steps which relate the temperature in the plurality of positions and the MVs. The MVs can further comprise one or any combination of a flow of naphthalene, a flow of orthoxylene, a flow of the oxygen comprising source gas, an evaporator temperature associated with the naphthalene or orthoxylene, and a salt bath temperature associated with the reactor. The dynamic model preferably coordinates movement the MVs with a quadratic program (QP) to meet user input control and optimization objectives, the objectives comprising the MVs and CVs.

BRIEF DESCRIPTION OF THE DRAWINGS

A fuller understanding of the present invention and the features and benefits thereof will be accomplished upon review of the following detailed description together with the accompanying drawings, in which:

FIG. 7 is a table that lists a plurality of manipulated variables (MVs) that can all be used with controllers according to the present invention.

FIG. 8 is a table that lists a plurality of controlled variables (CVs) and a disturbance variable (ambient temperature) that can all be used with multivariable controllers according to the present invention.

FIG. 10 is a screen dump of respective CVs during PA processing. Those with STATUS "GOOD" indicate that they are being actively monitored and automatically controlled by a controller running control methodology according to the present invention.

FIG. 11(a) is a screen dump of respective MVs (same eight MVs listed in FIG. 7) adjusted by and automatically controlled by a controller running control methodology according to the present invention to keep the CVs within respective specified limits.

FIG. 14 shows the moving average of PA product inventory over 1, 2 and 4 hours for a period of 2 days using a known controller running conventional control methodology as compared to a controller running control methodology according to the present invention. The average inventory on the right side of the plot (beyond the vertical line shown) is significantly higher than the inventory level at the beginning of the plot (conventional control) which shows a substantial increase in the PA production rate with the current invention implemented.

DETAILED DESCRIPTION

Figure 1:
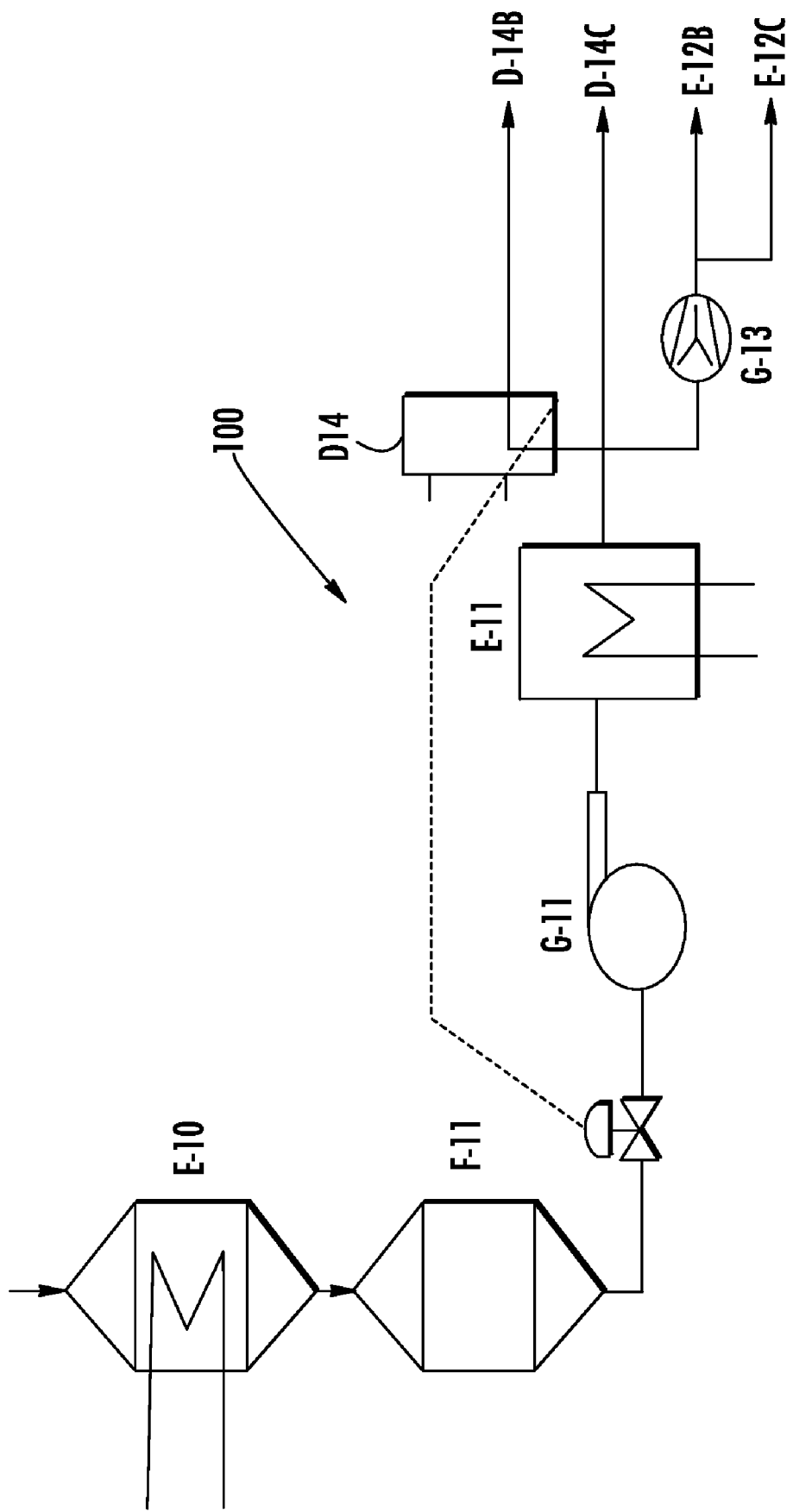
FIG. 1 is a simplified block diagram for an air blower and preheater section adapted for a conventional phthalic anhydride (PA) production unit.
Figure 2:
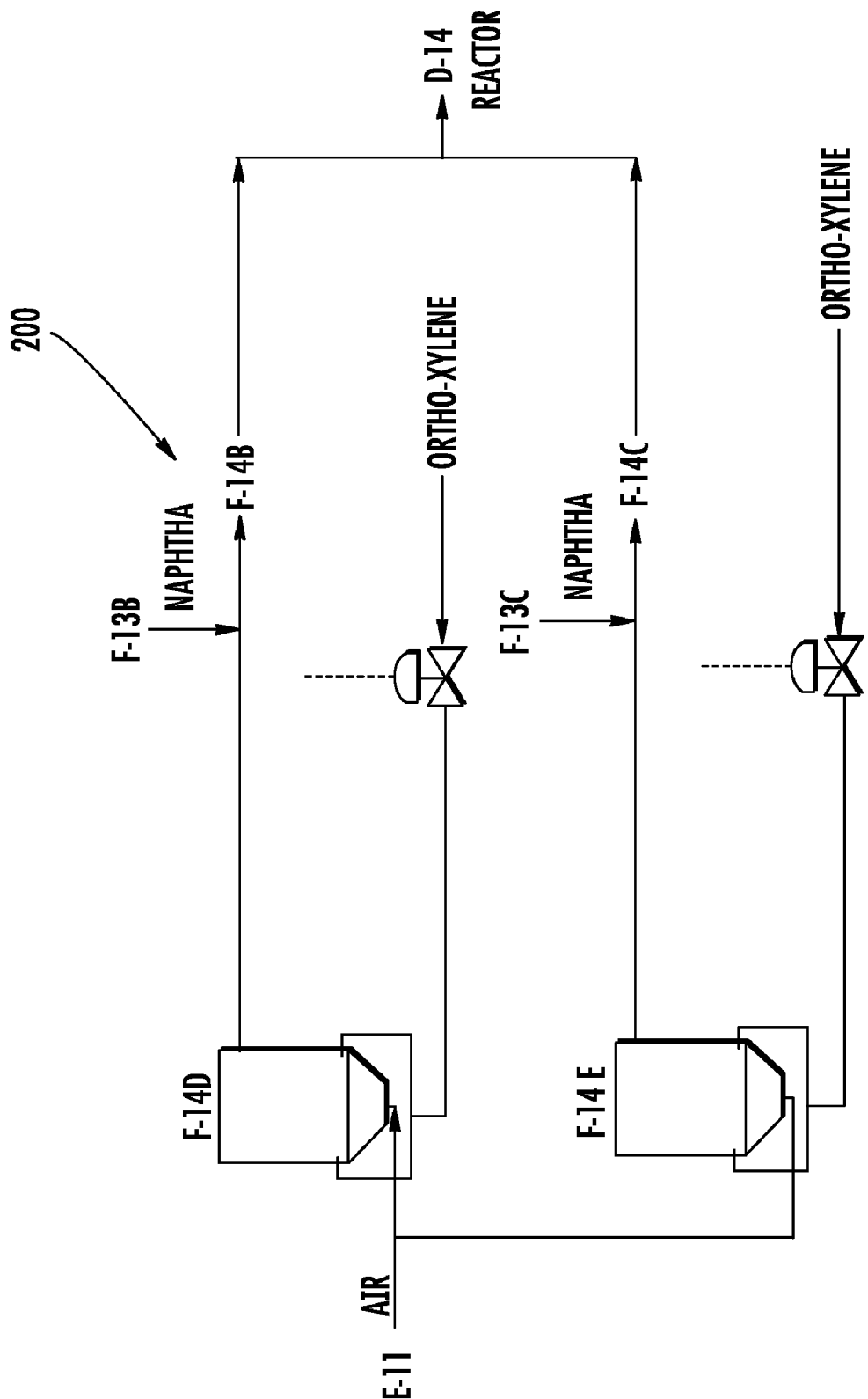
FIG. 2 is a simplified block diagram for an orthoxylene feed section adapted for a conventional PA production unit.
Figure 3:
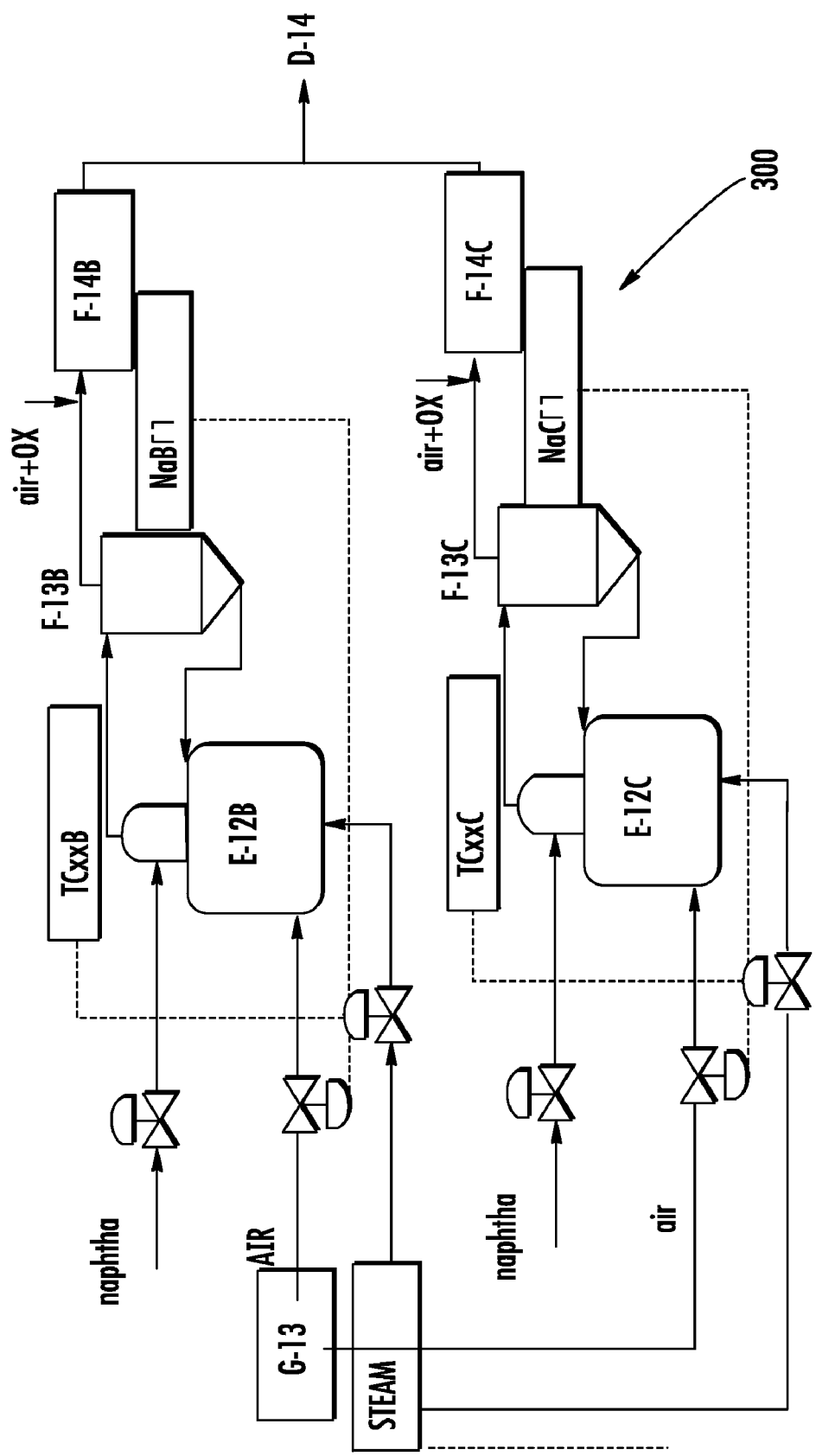
FIG. 3 is a simplified block diagram for a naphthalene feed section adapted for a conventional PA production unit.
Figure 4:
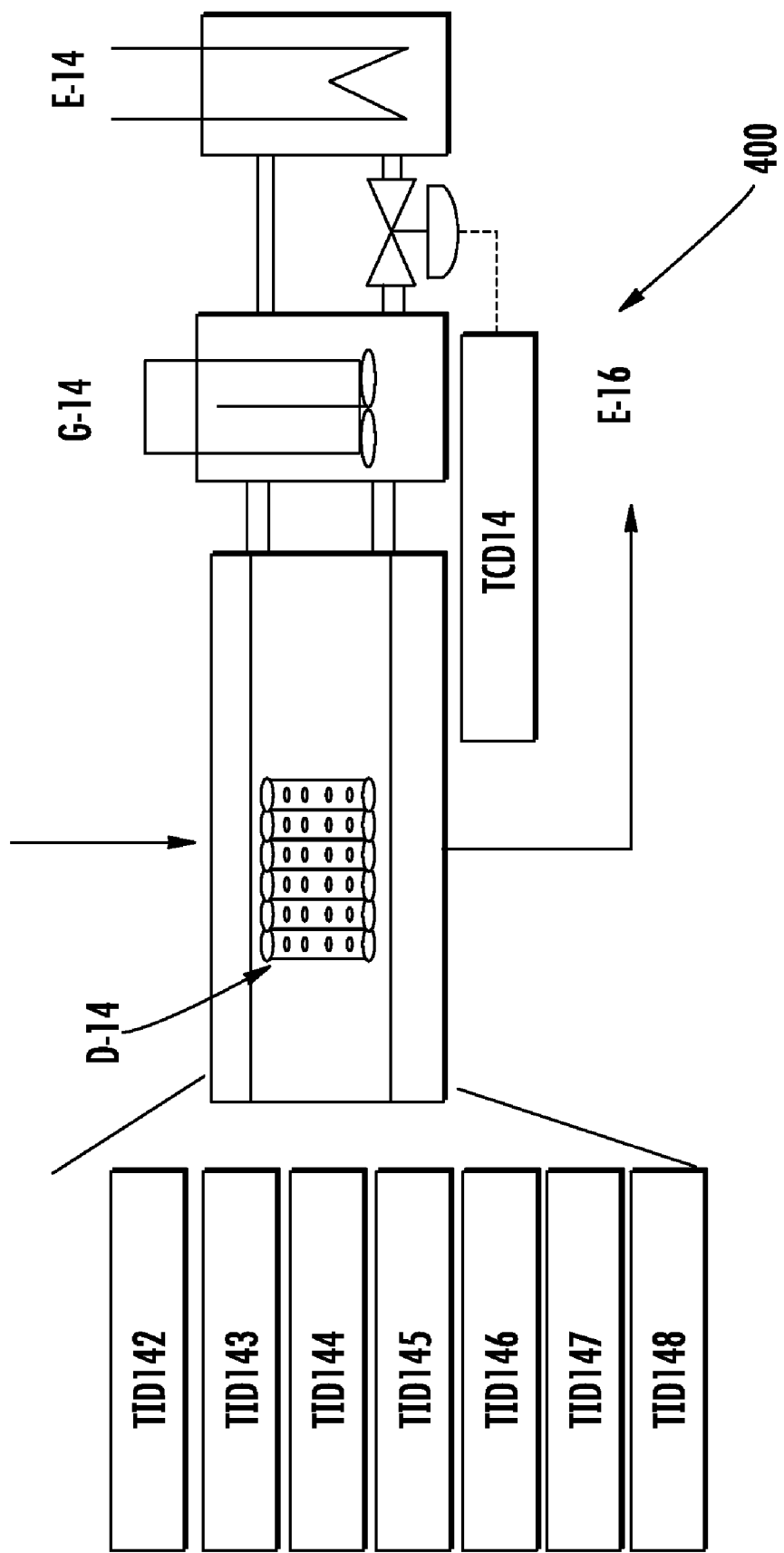
FIG. 4 is a simplified block diagram of a catalyzed oxidation reactor adapted for a conventional PA production unit.
Figure 5:
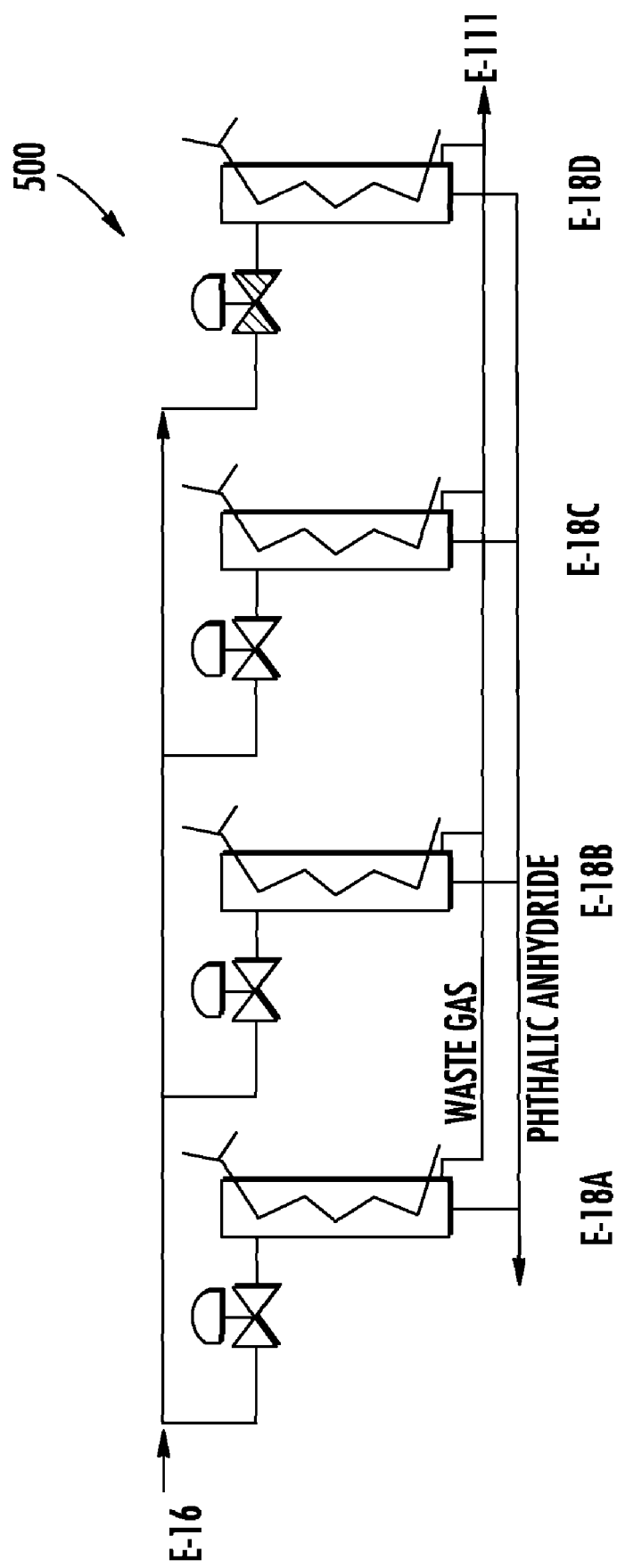
FIG. 5 is a simplified block diagram of a desublimation section adapted for a conventional PA production unit.
Figure 6:
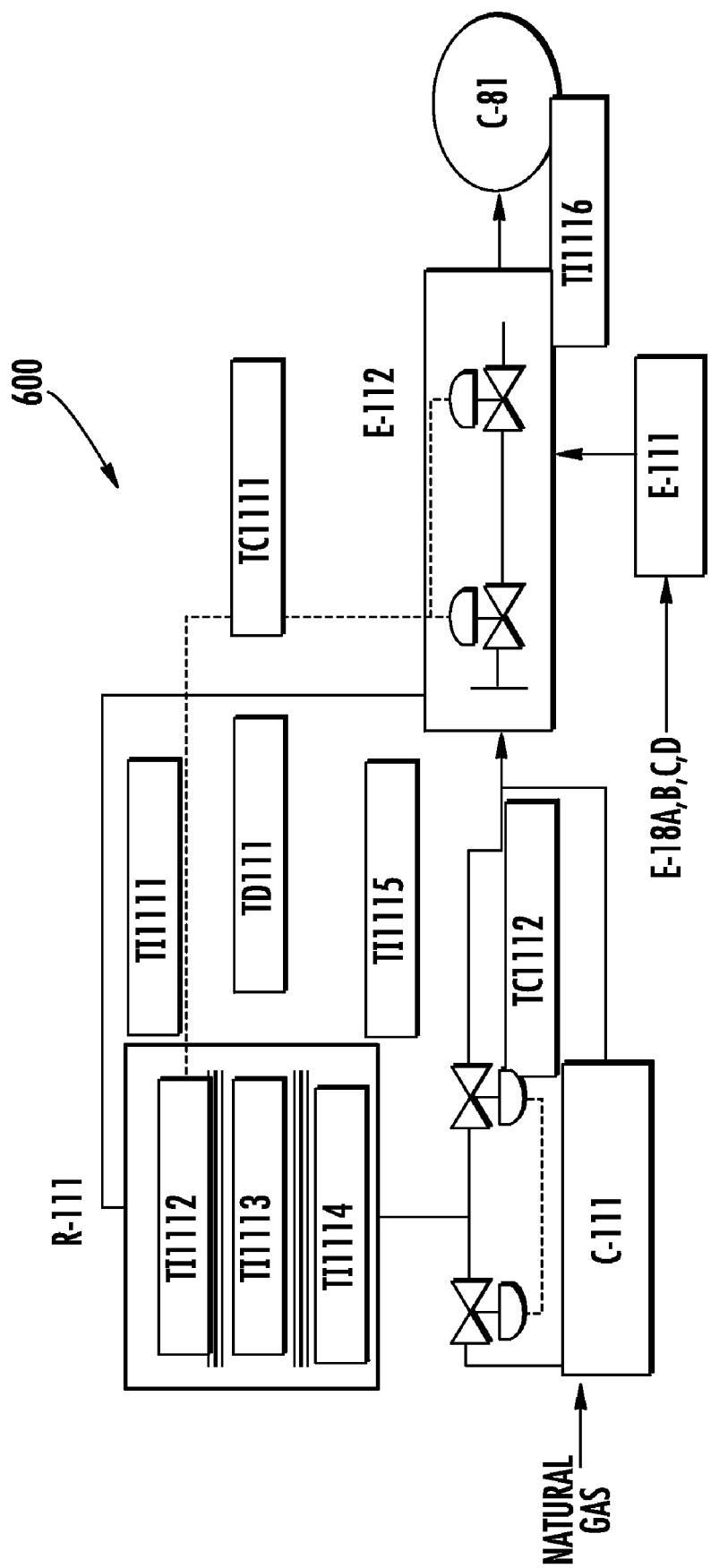
FIG. 6 is a simplified block diagram of a catalytic incineration of waste gas section adapted for a conventional PA production unit.

The present invention provides a multivariable process controller and related methodology for improved control of catalyzed chemical reactions which form functionalized aromatics, produced by production units including a chemical reactor including a plurality of pipes connected in parallel having inner surfaces affixed with at least one solid catalyst. The functionalized aromatic is described herein as being phthalic anhydride (PA), formed by the catalytic oxidation of substituted aromatics comprising orthoxylene or naphthalene, preferably both orthoxylene and naphthalene. However, multivariable process controllers and related methodologies according to the present invention are in no way limited to PA.

For example, besides PA, the controller and associated methodology according to the present invention can be used for other catalytic oxidations, such as oxidation of ethyl benzene with nitrous oxide and a Cr/gamma alumina catalyst to styrene (see Kustrowski et al. Catalyst Letters 2002, 80 (1-2), 1011-372x), Oxidation of beta-picoline with oxygen (air) and V—Ti oxide catalyst to nicotinic acid (see Holderich et al Pure Appl. Chem. 2000, 72 (7) 1273-87, and oxidation of benzene with nitrous oxide and an Fe/zeolite catalyst to phenol (see Holderich et al.).

The reactor forms the PA product by receiving flows of reagents including at least one oxidizable substituted aromatic and an oxygen including source gas (e.g. air) at one or more reactor inlets, generally located at a top of the reactor. Other arrangements are possible, such as receiving reagents at the bottom of the reactor. PA unit multivariable controllers according to the present invention simultaneously manipulate a set of independent variables (Manipulated Variables, or MVs) to maintain a set of dependent variables (Controlled Variables, or CVs) within constraints and/or targets (which can be entered and generally changed by the operator) using a dynamic multivariate process model. The dynamic multivariable model (control algorithm) for the process represents the effects of moving a plurality of MVs including a flow of an oxygen including source gas (e.g. air) and a flow and/or temperature of the oxidizable substituted aromatic reagent(s) on CVs including a temperature at a plurality of positions along a length of the catalyst lined pipes. The dynamic model preferably coordinates movement of the MVs with a quadratic program (QP) to meet user input control and optimization objectives, where the objectives can comprise MVs and CVs. However, depending on the operation preference, a linear program (LP) may also be used, or a solution comprising a mixture of LP and QP.

The multivariate process model used by multivariate controllers according to the present invention is generally generated in a process referred to herein as step-testing, which is typically based on a series of designed empirical tests. Using such tests, optimal temperatures for each of the active "layers" based on a given catalyst efficiency (which is generally based on age) can be derived. The plurality of positions along the length of the pipes, sometimes referred to as "layers", are really imaginary limits determining the reactor temperature profile from the top to the bottom of the reactor (temperature profile along the length of the pipes).

The tests are designed to derive the empirical models from plant data using system excitation with designed test signals that can be viewed as an extensive plant interview process. The tests are generally designed to reveal the relationship between the operating temperatures (estimated as being optimal by the manufacturing company representative/engineer) as well as other CVs and the MVs used by the operations and the process controller according to the present invention. Step testing is generally designed to be as flexible as possible. This means that at the discretion of the company representative/engineer more that one MV can be moved at a time to shorten the plant testing period. An important step is generally to not have the MVs be time correlated. All MV's, DV's, CV's and other plant variables are generally measured, collected and archived for off line model generation. Thus, the final design of multivariable controllers with respect to MVs, CVs, and measured variables is preferably determined after step-testing. However, it is may be possible to derive the dynamic model using appropriate simulation software, either presently available or becoming available in the future.

During the process, a first parameter related to performance of the catalyst in producing the PA product and a second parameter including a temperature at one or more of the plurality of positions along the length of the pipe is measured. FIGS. 7 and 8, respectively, provides an exemplary list of MVs and CVs which can all be measured parameters. Using the dynamic model, the temperature in the plurality of positions along the length of the reactor pipes are automatically adjustable based on at least the first measured parameter, which permits the temperature profile to be dynamically adjusted to compensate for ageing of the catalyst to improve production efficiency of PA and other products.

Figure 9:
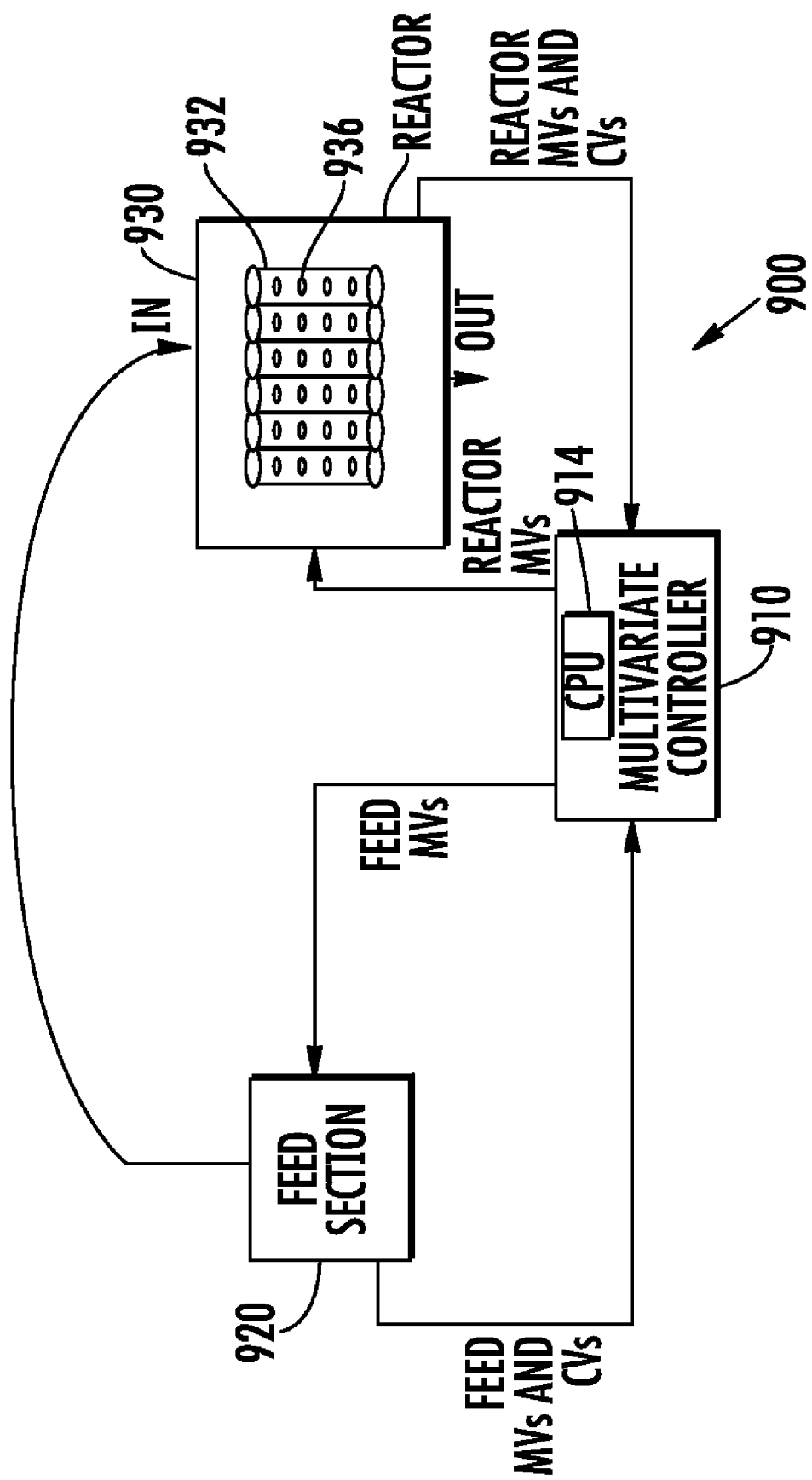
FIG. 9 is a block diagram showing a portion of a PA unit comprising a multivariable controller according to the present invention controlling a feed section and an oxidation reactor, along with the respective interconnections that permit the transfer of control signals and data.

Multivariable controllers according to the present invention can control a plurality of sections of the PA unit. FIG. 9 is a block diagram showing a portion of a PA unit 900 comprising a multivariable controller according to the present invention 910 controlling a feed section 920 and an oxidation reactor of the PA unit 930, along with the respective interconnections. Communicable connections are generally wired (electrical) connections. However, optical or over-the-air communications may also be used. Reactor 930 comprises a plurality of pipes connected in parallel 932 having inner surfaces affixed with at least one solid catalyst 936. Reagents from feed section 920 are shown directed into the top of reactor 930 (IN) and exit at the bottom (OUT) as indicated by the arrows shown. In the PA process, all reactants are pushed through the same inner pipe where the reactant oxidation will take place in the presence of the catalyst.

Multivariate controller 910 receives feed section MV and CV data from feed section 920 as well as MV and CV data from reactor 930, such as from suitable sensors, meters or other measurement devices. Multivariate controller 910 is generally CPU based, such as a microprocessor based CPU 914, and includes associated non-volatile writeable memory. The memory is generally used to store the dynamic model. The CPU 914 thus has an associated stored dynamic multivariable model for the process which represents the effects of moving a plurality of manipulated variables (MVs) comprising a flow of molecular oxygen comprising source gas and a flow or temperature of the oxidizable substituted aromatic on controlled variables (CVs) comprising a temperature at a plurality of positions along a length of the pipes.

A plurality of inputs comprising feed MVs and CVs and reactor MVs and CVs are communicably coupled to the CPU 914 of controller 910 thus receiving process information during the process. As noted above, the process information generally includes at least a first measured parameter related to performance of the catalyst in producing the PA product and a second measured parameter comprising the temperature at the plurality of pipe positions. The CPU 914 drives a plurality outputs by sending control signals to adjust the temperature in the plurality of pipe positions depending on at least the first measured parameter using the dynamic model. The first measured parameter can comprise conversion efficiency. Conversion efficiency is defined herein as the ratio between the product (e.g. PA) and the raw material used to produce the product excluding the air (or other oxygen source) intake.

The control algorithm implemented by control methodology according to the present invention preferably coordinates movement of the MVs with a quadratic program (QP) in order to meet the control and optimization objectives. The QP objective function reflects the operating objectives of the unit and is adjustable, preferably via operator input which allows operation engineers to modify the objective function as operating objectives change.

The present invention also preferably uses Model Predictive Control (MPC) which is widely adopted in industry to deal with large multivariable constrained control problems. The main idea of MPC is to choose the control action by repeatedly solving an optimal control problem. MPC aims at minimizing a performance criterion over a future horizon, possibly subject to constraints on the manipulated inputs and outputs, where the future behavior is computed according to a model of the plant or other system.

Model predictive controllers rely on dynamic models of the process, most often linear empirical models obtained by system identification. The models predict the behavior of dependent variables (i.e., outputs) of the dynamic system with respect to changes in the process independent variables (i.e., inputs). The MPC controller uses the models and current plant measurements to calculate future moves in the independent variables that will result in operation that honors all independent and dependent variable constraints. The MPC then sends this set of independent variable moves to the corresponding regulatory controller setpoints to be implemented in the process. Linear MPC approaches can be used in the majority of applications with the feedback mechanism of the MPC compensating for prediction errors due to structural mismatch between the model and the plant. MPC based-controllers according to the present invention can be linear or non-linear. In MPCs that utilize only linear models, the superposition principle of linear algebra enables the effect of changes in multiple independent variables to be added together to predict the response of the dependent variables. This simplifies the control problem to a series of direct matrix algebra calculations that are generally fast and robust.

Multivariable controllers according to the present invention generally provide all of the following:

i) Maintain the reactant concentration in the oxidizing reactor below its upper limit;

ii) maintain reactant concentration in the feed section below their low explosive limits;

iii) keep the turbo blower throughput below or at the operation specified upper limit;

iv) maintain the oxidation reactor catalyst temperatures within its safe limits;

v) maintain controller outputs within the operations specified limits, and vi) Maximize the crude PA production.

The present invention thus solves the need for improved conversion efficiency for forming PA by providing a multivariable controller and related control methodology that manipulates a set of MVs to maintain a set of CVs within constraints or targets. As noted above, such controllers provide suitable structure so that MVs and CVs can be user programmed and changed by the user. Operators will generally set target values and/or limits for key CVs and MVs. The flexibility of the solution is such way that operation engineers are capable of fixing the reactor catalyst temperature profile in any position along the reactor depending on the ageing stage. Maximum catalyst life time is generally about three to four years for PA catalysts.

Applied to PA production, unlike known controllers described in the Background of the present application, multivariable controllers and related multivariable control methodology according to the present invention allows PA unit maximization to continue after the first (and subsequent) constraint activation occurs that enables reaching more than one, and preferably all of a set of constraints, before PA maximization is stopped. The set of constraints can include a maximum air compressor flow, a maximum reactant concentration at the oxidation reactor inlet, a maximum orthoxylene concentration below low explosive level in the feeding section, a maximum naphthalene concentration above high explosive level in the feeding section, a maximum oxidation reactor catalyst temperature, and maximum waste gas catalytic incinerator differential temperature (outlet-inlet). It is noted that differential temperature was not included in the current implementation actually tested described below simply because the handle to control it was not readily accessible to the computer program. As noted above, in contrast, conventional PA units are controlled to end maximization after the first one of a plurality of maximization constraints is active (reached). Accordingly, a significant difference between the present invention and conventional controller technology is that after reaching the first constraint activation, controllers according to the present invention continue maximization after the first constraint is reached, which allows more than one and preferably all the constraints to be reached before process maximization is stopped. As a result, controllers according to the present invention provide significantly higher conversion efficiency.

Multivariable controllers according to the present invention can also make adjustment for a set of measured feedforward variables (Disturbance Variables, or DVs), such as the ambient temperature shown in FIG. 8. Ambient temperature is a DV since it is able to be measured but is not generally able to be controlled. Thus, the measuring values step preferably includes measuring an ambient temperature. The measuring parameters step generally includes measuring a flow of the oxygen comprising source gas. To reduce signal noise associated with measuring a flow of the oxygen comprising source gas, the measuring can further comprise the step of Kalman filtering.

Controllers according to the present invention are also capable of maintaining the residence time of the reagents in the reactor within a narrow range thus allowing the operation to adjust the residence time depending on the catalyst performance and properties. The residence time quantifies how fast the reactant material moves through the reactor. Moreover, the system maintains the operational design limits as well as the catalyst constraints within specified values by manipulating a plurality of MVs noted above. The solution provided by the present invention is configured to perform in satisfactory manner during the whole aging period of the PA catalyst, which as noted above is generally 3 to 4 years, where operating limits result in shifting from the upper part of the reactor to the lowest portion in terms of activity.

During pre-step sessions actually performed, the Inventors found certain parameters can be significantly noisy. For example, the air flow measurement was found to be very noisy (high standard deviation when the valve output was taken on manual). Consequently, since one of the main constraints according to the present invention is generally air flow throughput, signal noise prevents approaching its upper limit without too much violation unless special means are developed to decrease the measurement variability and improve air flow estimation. Kalman or other filtering can reduce signal noise.

The improved air flow estimation could be used also in the distributed control system (DCS) controller according to the present invention. Because traditional filter always introduce delays leading to detuned DCS control loops, alternative mechanisms can be used, such as statistical filters and model based filters, such as Kalman or other filtering.

Statistical filter rely on the statistics behavior to detect a change in the mean value or trend while model based filters use a priori process knowledge with measurement feedback to estimate the optimal process values. In general, statistical filters are used in the case the system is difficult to model.

The present invention is typically used as the primary controller for distributed control system (DCS) used in a manufacturing system, in which the controller elements are distributed throughout the system with each component sub-system controlled by one or more controllers. The entire system may be networked for communication and monitoring. The DCS generally uses computers (usually custom designed processors) as controllers and use both proprietary interconnections and protocols for communication. Input & output modules form component parts of the DCS. The processor receives information from input modules and sends information to output modules. The input modules receive information from input instruments in the process (field) and output modules transmit instructions to the output instruments in the field.

Control methodology according to the present invention can run on a variety of controller platforms, such as Honeywell's RMPCT™, running on a Honeywell APP Node™ (Honeywell International, Morris Township, N.J.). A single multivariable controller according to the invention can control multiple production unit sections, such as for the feed section 920 and the oxidation reactor 930 as shown in FIG. 9 and described above, and with adequate instrumentation other sections, such as the incineration section.

As noted above, although described relative to production units for forming PA, multivariate controllers according to the present invention are broadly applicable to other reactions that involve catalyst that experience degradation in their catalytic properties. For example the invention can be applied to maleic anhydride production units.

EXAMPLES

It should be understood that the Examples described below are provided for illustrative purposes only and do not in any way define the scope of the present invention.

FIGS. 10-14 represent data from actual implementation of a particular embodiment of the present invention, comprising screen dumps of main system variables with the inventive solution comprising a multivariate digital controller running control methodology according to the present invention in an actual PA production process. In some of these Figures, the data is comparative in nature and includes data obtained using a known controller running conventional control methodology and data from using a controller running control methodology according to the present invention to demonstrate the control improvement provided by the present invention. There are of two types of data provided: a tabular form showing a snapshot of all variables in this solution, specifically FIG. 10 for the exemplary controlled variables (CVs), FIGS. 11(a) and (b) for the exemplary manipulated variables (MVs), and time plots over a period of days showing the CVs and MVs on different FIGS. 12(a)-13(b). The CVs are kept within specified limits for various reasons, e.g. planning for the reactant flows, design reasons for the reactor temperatures, safety reason (explosive levels) regarding the concentration. The MVs are the handles the operator uses to keep the CVs within their specification. They are simultaneously calculated by the computer program associated with multivariate digital controllers according to the present invention and generally sent to DCS for implementation.

Figure 11B:
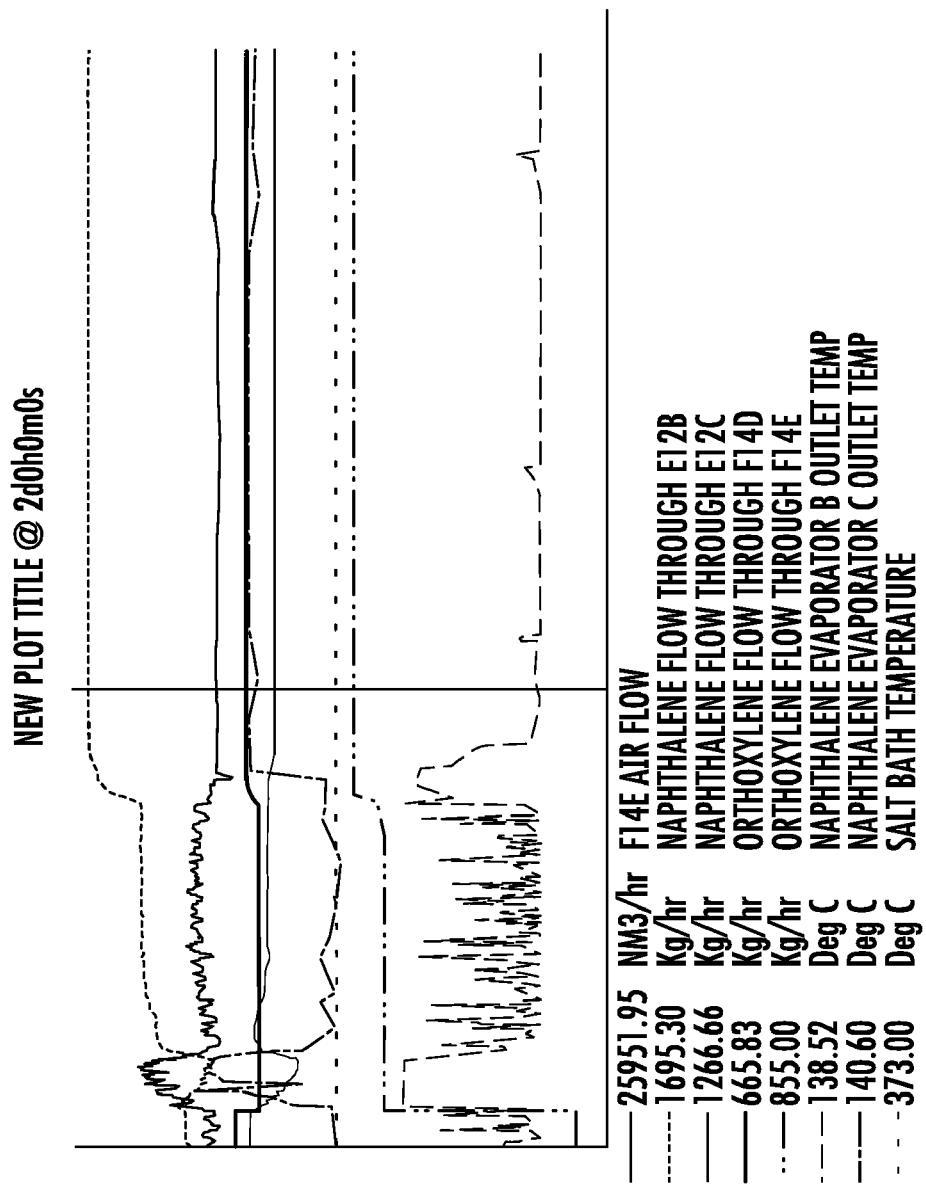
FIG. 11(b) is a time plot showing the set of eight MVs (same eight MVs listed in FIG. 7) plotted using a known controller running conventional control methodology as compared to a controller running control methodology according to the present invention. There is a clear behavior distinction at the left side of the plot one (conventional control) and the right side of the plot (beyond the vertical line shown) where the controller running control methodology according to the present invention is active.

FIG. 10 is a screen dump of the controlled variables during PA processing. Those with STATUS "GOOD" indicate that they are being actively monitored and automatically controlled by a controller running control methodology according to the present invention. FIG. 11(a) is a screen dump of the manipulated variables adjusted by and automatically controlled by a controller running control methodology according to the present invention to keep the controlled variables within respective specified limits. FIG. 11(b) is a time plot showing the set of manipulated variables the computer program adjusts to keep the controlled variables within the specified limits. There is a clear behavior distinction at the left side of the plot one (conventional control) and the right side of the plot (beyond the vertical line shown) where the controller running control methodology according to the present invention was active.

Figure 12A:
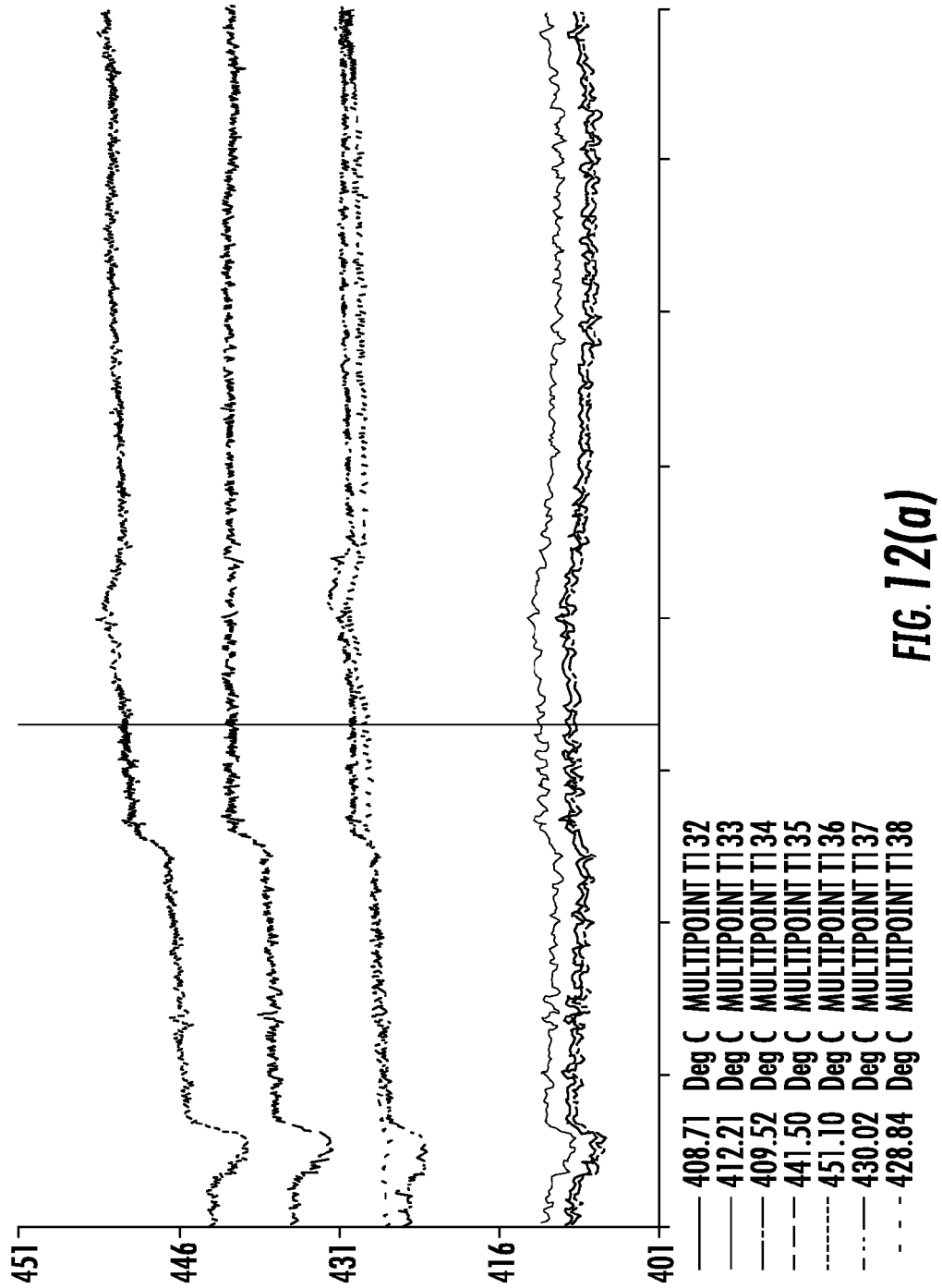
FIG. 12(a) is a plot of the reactor temperatures, which are a subset of the CVs, demonstrating time behavior using a known controller running conventional control methodology as compared to a controller running control methodology according to the present invention. There is a clear behavior distinction at the left side of the plot one (conventional control) and the right side of the plot (beyond the vertical line shown) where the controller running control methodology according to the present invention is active.

FIG. 12(a) is a plot of the reactor temperatures, which are a subset of the CVs, demonstrating time behavior using a known controller running conventional control methodology as compared to a controller running control methodology according to the present invention. There is a clear behavior distinction at the left side of the plot one (conventional control) and the right side of the plot (beyond the vertical line shown) where the controller running control methodology according to the present invention is active.

Figure 12B:
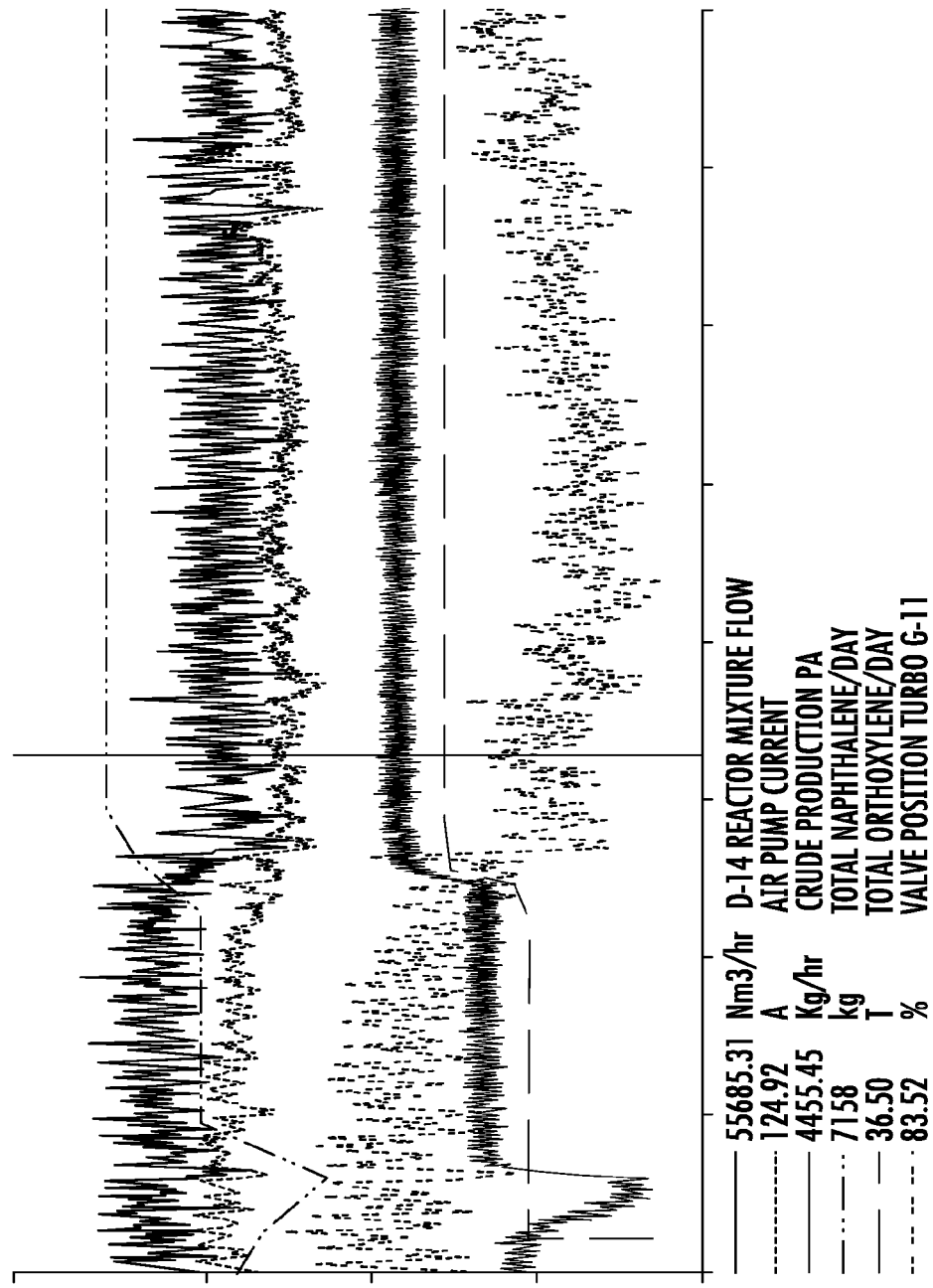
FIG. 12(b) is a plot showing the main reactor flows such as the air and the reactant flows using a known controller running conventional control methodology as compared to a controller running control methodology according to the present invention. There is a clear behavior distinction at the left side of the plot one (conventional control) and the right side of the plot (beyond the vertical line shown) where the controller running control methodology according to the present invention is active.

FIG. 12(b) is a plot showing the main reactor flows such as the air and the reactant flows using a known controller running conventional control methodology as compared to a controller running control methodology according to the present invention. There is a clear behavior distinction at the left side of the plot one (conventional control) and the right side of the plot (beyond the vertical line shown) where the controller running control methodology according to the present invention is active.

Figure 13A:
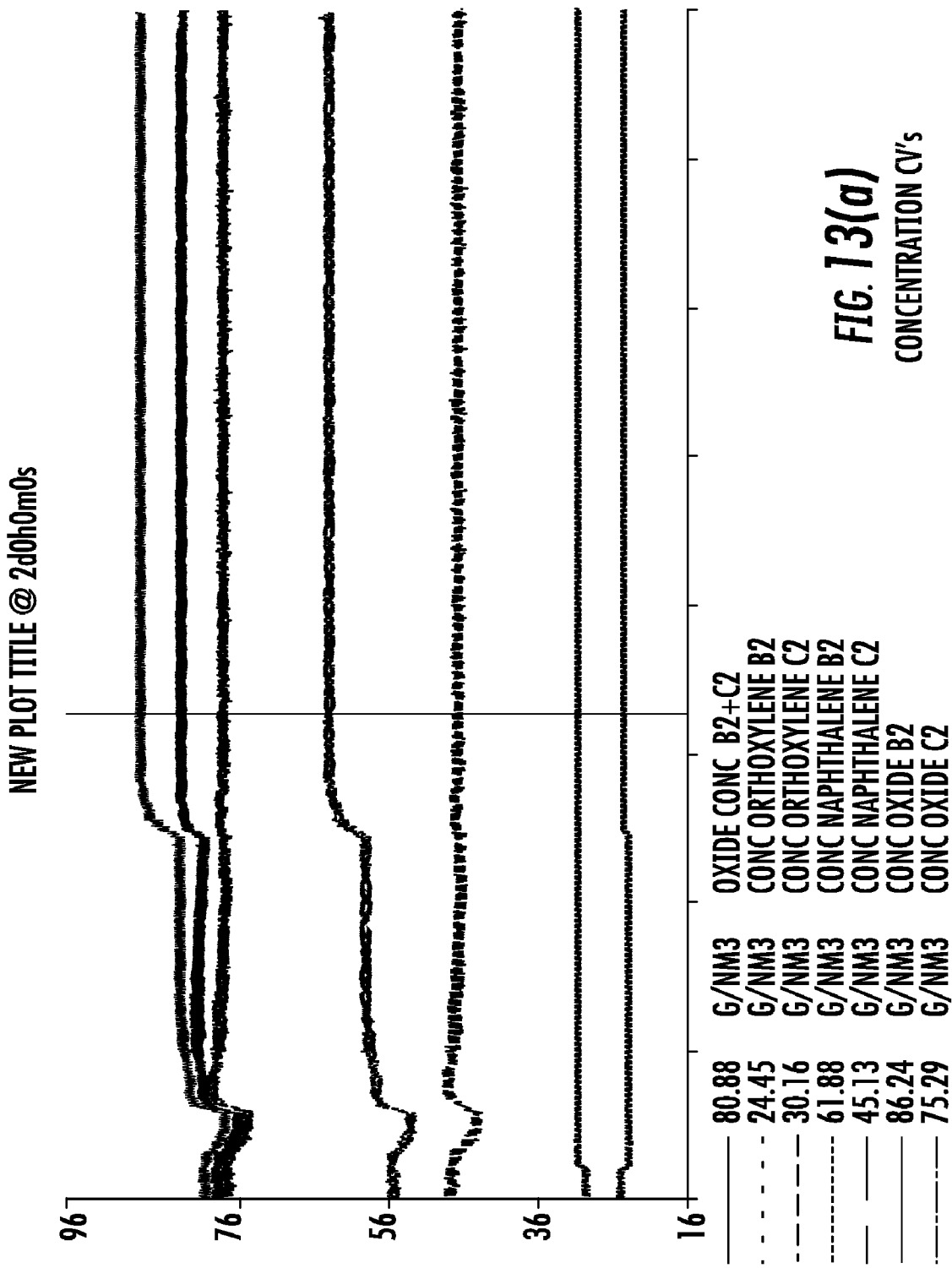
FIG. 13(a) shows reactants being diluted by air at different sections of the feed system and their respective concentrations graphically illustrated using a known controller running conventional control methodology as compared to a controller running control methodology according to the present invention. There is a clear behavior distinction at the left side of the plot one (conventional control) and the right side of the plot (beyond the vertical line shown) where the controller running control methodology according to the present invention is active.

FIG. 13(a) shows reactants being diluted by air at different sections of the feed system and their respective concentrations graphically illustrated using a known controller running conventional control methodology as compared to a controller running control methodology according to the present invention. There is a clear behavior distinction at the left side of the plot one (conventional control) and the right side of the plot (beyond the vertical line shown) where the controller running control methodology according to the present invention is active.

Figure 13B:
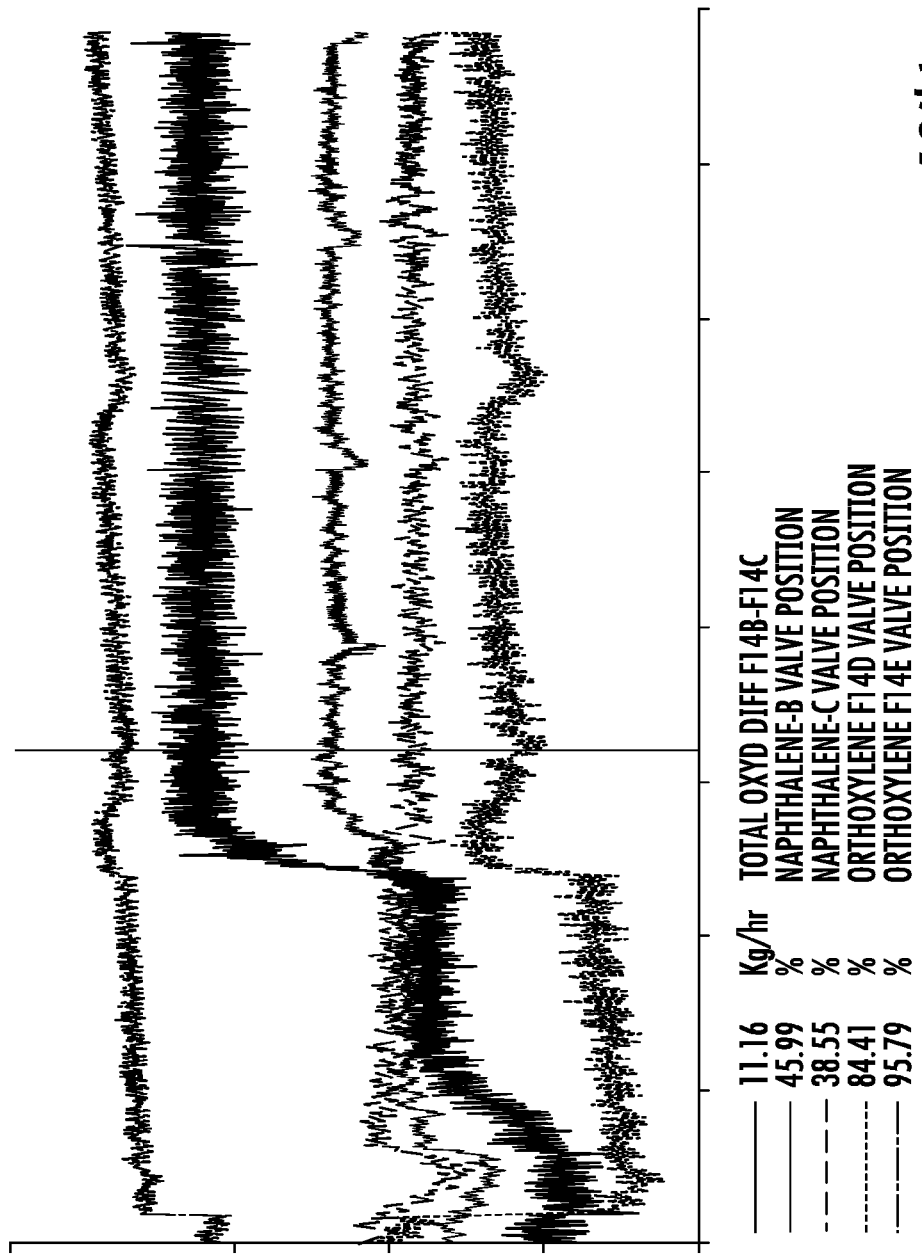
FIG. 13(b) is a time plot of main valve positions identified as constraints in the present application using a known controller running conventional control methodology as compared to a controller running control methodology according to the present invention. These valve positions are kept within a control range maintain the system controllability. There is a clear behavior distinction at the left side of the plot one (conventional control) and the right side of the plot (beyond the vertical line shown) where the controller running control methodology according to the present invention is active.

FIG. 13(b) is a time plot of main valve positions identified as constraints in the present application using a known controller running conventional control methodology as compared to a controller running control methodology according to the present invention. These valve positions are kept within a control range maintain the system controllability. There is a clear behavior distinction at the left side of the plot one (conventional control) and the right side of the plot (beyond the vertical line shown) where the controller running control methodology according to the present invention is active.

FIG. 14 shows the moving average of PA product inventory over 1, 2 and 4 hours for a period of 2 days using a known controller running conventional control methodology as compared to a controller running control methodology according to the present invention. The average inventory on the right side of the plot (beyond the vertical line shown) is significantly higher than the inventory level at the beginning of the plot (conventional control) which shows a substantial increase in the PA production rate with the current invention implemented.

In the preceding description, certain details are set forth in conjunction with the described embodiment of the present invention to provide a sufficient understanding of the invention. One skilled in the art will appreciate, however, that the invention may be practiced without these particular details. Furthermore, one skilled in the art will appreciate that the example embodiments described above do not limit the scope of the present invention and will also understand that various modifications, equivalents, and combinations of the disclosed embodiments and components of such embodiments are within the scope of the present invention.

Moreover, embodiments including fewer than all the components of any of the respective described embodiments may also within the scope of the present invention although not expressly described in detail. Finally, the operation of well known components and/or processes has not been shown or described in detail below to avoid unnecessarily obscuring the present invention.

One skilled in the art will understood that even though various embodiments and advantages of the present Invention have been set forth in the foregoing description, the above disclosure is illustrative only, and changes may be made in detail, and yet remain within the broad principles of the invention. For example, some of the controller components described above may be implemented using either digital or analog circuitry, or a combination of both, and also, where appropriate may be realized through software executing on suitable processing circuitry. The present invention is to be limited only by the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the following claims.

I claim:

1. A multi variable process controller for controlling a catalyzed chemical reaction performed in a production unit including a reactor feed section and a chemical reactor comprising a plurality of pipes connected in parallel having inner surfaces affixed with at least one solid catalyst, said reactor implementing a process for forming a phthalic anhydride (PA) product, comprising:

receiving controlled flows of reagents including at least one oxidizable substituted aromatic and an oxygen comprising source at an at least one inlet of said reactor:

a CPU having a stored dynamic multi variable model for said process which represents the effects of moving a plurality of manipulated variables (MVs) comprising a flow of said oxygen comprising source gas and a flow or temperature of said oxidizable substituted aromatic on controlled variables (CVs) comprising a temperature at a plurality of positions along a length of said pipes:

a plurality of inputs coupled to said CPU for receiving process information during said process comprising a first measured parameter related to performance of said catalyst in producing said PA product and a second measured parameter comprising said temperature at said plurality of positions, and and a plurality outputs driven by said CPU for sending control signals to adjust said temperature in said plurality of positions depending on at least said first measured parameter using said dynamic model.

2. The process controller of claim 1, wherein said first measured parameter comprises conversion efficiency into said product.

3. The process controller of claim 2, wherein said process controller controls a residence time of said reagents in said reactor by minimizing a flow rate of said oxygen comprising source gas and maintaining a sufficient flow rate of said oxygen comprising source gas to achieve a predetermined minimum for said conversion efficiency.

4. The process controller of claim 3, wherein said process information further comprises an ambient temperature.

5. The process controller of claim 1, wherein data to compile said model is derived in part by test steps which relate said temperature in said plurality of positions and said MVs.

6. The process controller of claim 1, wherein said MVs further comprise at least one selected from the group consisting of a flow of said naphthalene, a flow of said orthoxylene, a flow of said oxygen comprising source gas, an evaporator temperature associated with said naphthalene or said orthoxylene, and a salt bath temperature associated with said reactor.

7. The process controller of claim 1, wherein said dynamic model meets user input control and optimization objectives, said objectives comprising said MVs and said CVs.

* * * * *